United States Patent [19]

Hall et al.

[11] 4,104,270

[45] Aug. 1, 1978

[54] PROCESS FOR THE MANUFACTURE OF AROMATIC PHOSPHONATES

[75] Inventors: Nigel Hall; Raymond Price; Philip Martin Rowbotham, all of Manchester, England

[73] Assignee: Imperial Chemical Industries Limited, London, England

[21] Appl. No.: 777,648

[22] Filed: Mar. 15, 1977

[30] Foreign Application Priority Data

Apr. 26, 1976 [GB] United Kingdom ............... 16778/76
May 27, 1976 [GB] United Kingdom ............... 22053/76

[51] Int. Cl.² .................... C07C 107/06; C07F 9/40
[52] U.S. Cl. ................................ 260/205; 260/267.1; 260/969; 260/970; 260/961
[58] Field of Search ................ 260/970, 969, 961; 200/205, 207.1

[56] References Cited

U.S. PATENT DOCUMENTS

3,493,639   2/1970   Tavs ............................... 260/969
3,705,214   12/1972  Martin ............................ 260/969

OTHER PUBLICATIONS

Arbuzov et al, "Bull. Acad. Sic. U.S.S.R., Div. Chem. Sci." English translation, (1962), pp. 755–758.

*Primary Examiner*—Anton H. Sutto
*Attorney, Agent, or Firm*—Cushman, Darby & Cushman

[57] ABSTRACT

A process for the manufacture of aromatic phosphorus derivatives of the formula:

$$Ar.PO(OR)_2 \qquad (1)$$

where R is an optionally substituted alkyl, alkenyl, aralkyl, cycloalkyl or aryl radical, and Ar is an aromatic radical linked to the phosphorus atom through a carbon atom of the aromatic radical which comprises contacting a phosphorous acid diester of the formula:

$$HO.P(OR)_2 \qquad (2)$$

with an aromatic halide of the formula Ar—X in the presence of copper or a copper compound, the symbols R and Ar having the meanings stated above and X representing a halogen atom.

The aromatic radical preferably contains an atom or group activating the halogen atom. The process provides an improved method for manufacture of the phosphonic acid diesters.

11 Claims, No Drawings

PROCESS FOR THE MANUFACTURE OF AROMATIC PHOSPHONATES

This invention relates to a new process for the manufacture of aromatic phosphorus compounds.

The manufacture of alkyl phosphonic acid esters by reaction of alkyl or benzyl halides with the sodium derivatives of di-alkyl esters of phosphorus acid is well known. It is also known that attempts to react most aromatic halides in a similar way give rise to very poor yields of the corresponding aromatic phosphonic acid esters accompanied by products arising from side-reactions.

The present invention provides a process for the manufacture of aromatic phosphorus derivatives of the formula

   (1)

where R is an optionally substituted alkyl, alkenyl, aralkyl, cycloalkyl or aryl radical, and Ar is an aromatic radical linked to the phosphorus atom through a carbon atom of the aromatic radical which comprises contacting a phosphorous acid diester of the formula:

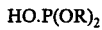   (2)

with an aromatic halide of the formula Ar—X in the presence of copper or a copper compound, the symbols R and Ar having the meanings stated above and X representing a halogen atom.

The process of the invention uses preferably an aromatic halide in which the carbon-halogen bond is activated by an atom or group so structurally connected to the carbon atom as to have an electron-withdrawing effect.

Groups which have an electron-withdrawing effect when attached to an aromatic nucleus include, for example:

nitro
alkyl- or aryl-sulphone
sulphonic acid and esters and amides thereof
carboxylic acid and esters and amides thereof
phosphonic acid esters and amides thereof
alkyl, cycloalkyl, aralkyl, aryl phosphinic acids and esters
and amides thereof,
halogen
cyano
carbonyl groups
arylazo groups, and
trifluoromethyl and as is well known, these groups have a greater effect when placed in o- or p-position of a carbocyclic aromatic ring carrying the halogen atom or which are linked to the carbon carrying the halogen atom through a conjugated double-bond system in the case of fused aromatic rings.

Atoms which can activate the C-halogen bond are, e.g., the nitrogen atom or atoms in pyridine, pyrimidine and s-triazine compounds having a halogen atom o or p to the nitrogen. Such effects can be augmented by substituent groups of the kind indicated above, e.g., as in a 3-halo-2-nitrofuran, pyrrole or thiophene.

As specific examples of aromatic halides which can be used there may be mentioned halogenated compounds of the benzene series, e.g., iodobenzene,
2,4-dinitro-chloro-, bromo- and iodo-benzenes,
2,4,6-trinitro-chloro, bromo- and iodo-benzenes,
2-nitro-4-trifluoromethylchloro-, bromo- and iodo-benzenes
2,4-dichloro-,-2,4-dibromo- and 2,4-diiodo-5-trifluoromethylnitrobenzenes,
2,4-dichloro-,-2,4-dibromo- and 2,4-diiodo-5-trifluoromethylnitrobenzenes,
2-nitro-4-cyano-chloro-, bromo- and iodo-benzenes
2-chloro-, 2-bromo- and 2-iodo-5-nitrobenzoic acids,
4-chloro-, 4-bromo- and 4-iodo-3,5-dinitrobenzoates,
ethyl-2-chloro-, 2-bromo- and 2-iodo-5-nitrobenzoates,
ethyl-4-chloro-, 4-bromo- and 4-iodo-3,5-dinitrobenzoates
1,4-dichloro-, 1,4-dibromo- and 1,4-diiodo-2,6-dinitrobenzenes,
2,6-dinitro-4-ethylsulphonylchloro-, bromo and iodobenzenes,
methyl 4-chloro-, 4-bromo- and 4-iodo 3,5-dinitrobenzene sulphonates,
4-chloro-, 4-bromo- and 4-iodo-3-nitrobenzophenones,
4-chloro-3,5-dinitroacetophenones,
3,3'-dichloro-, 3,3'-dibromo- and 3,3'-diiodo-4,4'-dinitrodiphenyls,
3,3'-dichloro,-3,3'-dibromo- and 3,3'-diiodo-2,2', 4,4'-tetranitrodiphenyls,
dimethyl 3,3'-dichloro,3,3'-dibromo- and 3,3'-diiodo-, 4,4'-dinitrodiphenyl-2,2'-disulphonates,
3,3'-dichloro-,-3,3'-dibromo- and 3,3'-diiodo-4,4'-dinitrodiphenylmethanes,
2,2-bis-(3-chloro-, 3-bromo- and 3-iodo-4-nitrophenyl)propanes,
3,3'-dichloro-, 3,3'-dibromo- and 3,3'-diiodo 2,2', 4,4'-tetranitrodiphenylmethanes,
3,3'-dichloro-, 3,3'-dibromo- and 3,3'-diiodo 2,2'-dicyano-4,4'-dinitrodiphenylmethanes,
3,3'-dichloro-, 3,3'-dibromo- and 3,3'-diiodo 4,4'-dinitro-5,5'-dimethoxycarbonyldiphenylmethanes,
2,2-bis-(3-chloro, 3-bromo- and 3-iodo-4-nitro-5-methoxycarbonylphenyl)propanes,
3,3'-dichloro,-3,3'-dibromo- and 3,3'-diiodo-4,4'-dinitrophenylsulphones,
1,3-dinitro-2,6-dichloro-,2,6-dibromo- and 2,6-diiodonaphthalenes.

Halogenated compounds of the naphthalene or anthacene series, e.g., methyl 2-chloro-, 2-bromo- and 2-iodo-1,5-dinitronaphthalene-4-sulphonates,
1,4-dinitro-2-chloro-, 2-bromo- and 2-iodo-anthraquinones,
1-chloro, 1-bromo- and 1-iodo-4-nitroanthraquinone-2-carboxylic acids,
1-chloro-, 1-bromo- and 1-iodo-anthraquinones
1-amino-4-chloro-, 4-bromo- and 4-iodo-anthraquinone-2-sulphonic acids
2-nitro-3-chloro-, 3-bromo- and 3-iodopyridines.

Halogenated aromatic heterocyclic compounds, more especially halogenated compounds containing a 5- or 6-membered aromatic heterocyclic ring, e.g., of the pyridine, pyrrole, furan or thiophene series, e.g., 2-chloro-, 2-bromo- and 2-iodo-pyridines,
2-nitro-3-chloro-, 3-bromo- and 3-iodo-pyrroles,
2-nitro-3-chloro-, 3-bromo- and 3-iodo-furans,
2-nitro-3-chloro-, 3-bromo and 3-iodo-thiophenes.

The new process is particularly useful for the introduction of a phosphonic acid ester group into the o-position of an azo group in aromatic azo compounds.

This reaction can be effected by using as aromatic compound, an azo compound of the formula:

$$Ar' - N = N - E \qquad (3)$$

in which Ar' represents a benzene or naphthalene radical having a halogen, i.e., F, Cl, Br or I, atom in ortho position of the azo group and which can carry further substituents, especially those which activate the C-halogen bond as described above, and E represents the radical of a coupling component which preferably carries a donor group ortho to the azo group.

The resulting compounds have the formula:

$$(RO)_2PO.Ar'' - N = N - E \qquad (4)$$

in which Ar'' is a o-arylene radical of the benzene or naphthalene series and the symbols R and E have the meanings stated above.

As examples of radicals represented by Ar', there may be mentioned:

2-chlorophenyl,
2-bromophenyl,
2-iodophenyl,
2-chloro-4-nitrophenyl,
2-bromo-4-cyanophenyl
2,6-dichloro-4-nitrophenyl,
4,6-dinitro-2-chlorophenyl,
2-bromo-4-nitrophenyl,
2-bromo-4-nitro-6-methylsulphonylphenyl,
2,6-dibromo-4-nitrophenyl, and
2-bromo-4,6-dinitrophenyl.

As examples of donor groups present in E, there may be mentioned, e.g., hydroxyl, amino, alkylamino, carboxylic acid, acylamino, alkylsulphonylamino, arylsulphonylamino, aralkylsulphonylamino, aryl amino or the donor atom may be a member of a heterocyclic ring as e.g., the heterocyclic N atom in pyridylazo and quinol-8-ylazo.

Thus as examples of coupling component radicals represented by E, there may be mentioned radicals of the following which couple in o-position to a donor group:

naphthols,
naphthol sulphonic acids,
aminonaphthol sulphonic acids,
o- coupling amines of the benzene or naphthalene series
p- substituted phenols
acylarylamides
pyrazolones
2-aminopyridones
2-hydroxypyridones p- coupling amines of the benzene or naphthalene series which contain a donor atom o to the coupling position, e.g., m-aminoacetanilides.

As particular examples of groups represented by E, there may be mentioned:

2-hydroxynaphth-1-yl
4-diethylamino-2-acetylaminophenyl
4-diethylamino-2-acetylamino-5-methoxyphenyl,
5-sulpho-4-diethylamino-2-acetylaminophenyl
5-sulpho-4-amino-2-acetylaminophenyl,
2-hydroxy-6-sulpho-naphth-1-yl,
2-hydroxy-6,8-disulpho-naphth-1-yl, and
1-hydroxy-8-amino-3,6-disulpho-naphth-2-yl The compounds of formula (2) are di-esters of phosphorous acid, in which as examples of groups represented by R, there may be mentioned: alkyl groups, preferably lower alkyl groups by which is meant groups containing up to 4 carbon atoms, and which may carry substituents, e.g., alkoxy groups, e.g., γ-methoxypropyl and β-ethoxyethyl, cycloaliphatic groups, e.g., cyclohexyl or 1- or 2-methyl-cyclohexyl, araliphatic groups, e.g., benzyl, aryl groups, e.g., 1- and 2-naphthyl, and diphenyl, but more especially phenyl, which may be substituted, e.g., by methyl, tert-butyl, methoxy, chloro and dimethylamino.

Thus as specific examples of compounds of formula (2), there may be mentioned:

dimethylphosphite,
diethylphosphite,
di-tert butylphosphite
diphenylphosphite
di(2-methoxyethyl)phosphite The copper present in the reaction mixture may be present as the free metal or as an alloy, or as a cuprous or cupric salt of an inorganic or organic acid or a salt of a complex ion containing copper. As examples of copper compounds which may be used, there may be mentioned:

cuprous chloride and bromide
cupric chloride
copper bronze,
cuprous acetate,
cuprous benzoate,
cuprous iodide
cupric sulphate
cupric acetate
tetrakis acetonitrile cuprous chloride,
tetrakis acetonitrile cuprous trifluoromethyl sulphonate and
tetrakis acetonitrile cuprous perchlorate The new reaction can conveniently be carried out by stirring together a mixture of the reactants and the copper in a solvent for a period of time and at a temperature which will depend on the ease with which the halogen atom is replaced by the phosphorus-containing group

—PO(OR)$_2$ during the course of the reaction. Usually a temperature between 0° and 80° C will be appropriate although other temperatures may be used if desired. It is preferred to use 1 gram atom of copper or the corresponding amount of a copper compound for each mole of the aromatic halide although lesser amounts are effective.

It is also preferred to use an excess of the phosphorus compound of formula (2) e.g., up to 3.0 moles per mole of the aromatic halide.

As solvents which may be used there may be mentioned:

aliphatic hydrocarbons, e.g., petroleum ether and white spirit,
aromatic hydrocarbons, e.g., toluene, chlorobenzene and nitrobenzene,
tetrahydrofuran,
acetonitrile,
dimethylformamide,
esters, e.g., ethyl acetate, but more especially alkanols or mono-etherified alkandiols, e.g., methanol, ethanol, n-and-i-propanols and t-butanols and $\beta$-ethoxyethanol In such cases, it is found advisable to use the alcohol R.OH corresponding to the group OR present in the phosphorus compound of formula (2). If an alcohol containing a different OR group is used, the product obtained can be a mixture containing small amounts of by-products formed by replacement of the OR group attached to the phosphorus atom by that present in the alcohol, or if the phosphorus compound of formula (2) is diphenylphosphite, the group OR in the resulting product of formula (1) is not phenyl but the radical corresponding to the alcohol used. This extremely facile ester-exchange reaction can be used deliberately for synthesis of the dialkyl esters of the phosphonic acids of formula (1) in cases where diphenyl phosphite is more easily available or prepared than the dialkyl phosphite which would otherwise be used.

The reaction product can contain as impurities compounds of the formula Ar.H and those of the formula Ar.Ar. The first of these is associated with reaction conditions containing protons, e.g., owing to liberation of hydrogen halide during the course of the reaction, or by interaction of the phosphorous acid diester with some copper compounds, e.g., cupric acetate, in the presence of water. The second impurity appears to be associated with the use of copper metal as catalyst.

The preferred conditions are to use a hydroxylic solvent ROH, together with a catalytic amount of cuprous iodide and an acid-binding agent, e.g. a tertiary amine of strongly basic character e.g., triethylamine or tri-n-propylamine, or the sodium or potassium salt of a weak acid, e.g., acetic acid, in sufficient quantity to neutralise the liberated hydrogen halide. Under these conditions, reaction proceeds quickly to give a product remarkably free from impurities.

The products can be isolated from the reaction mixture by treating the reaction mixture with water, preferably after removal of any water-immiscible solvent, to decompose any residual starting phosphorus compound of formula (2).

The products of formula (1) have a variety of uses, but in particular, they are useful as a source of aromatic phosphonic acids, obtainable by hydrolysing by heating with aqueous acid, e.g., 5N (i.e., 18–20% by weight) hydrochloric acid; in this case mixtures of products of formula (1) obtained as mentioned in an earlier paragraph give rise to a single phosphonic acid and are as useful for this purpose as any of the constituents of the mixture.

The invention is illustrated by the following Examples in which parts and percentages are by weight:

EXAMPLE 1

A stirred mixture of 3-acetylamino-4-(2'-bromo-4',6'-dinitro phenylazo)-N,N-diethylaniline (1 part), diethyl phosphite (0.44 part), sodium acetate trihydrate (0.58 part) and ethanol (33 parts) was boiled under reflux for 5 minutes. Cuprous iodide (0.08 parts) was then added and the mixture was boiled under reflux for 1 hour. The mixture was cooled and the product was separated by filtration, washed with water and crystallized from ethanol to give 1.03 parts of diethyl-3,5-dinitro-2-[2'-acetylamino-4'-N,N-diethyl amino phenylazo]phenyl phosphonate.

Found: C, 49.3%; H, 5.2%; N, 15.7%; P, 5.7%. $C_{22}H_{29}N_6O_8P$ requires: C, 49.15%; H, 5.45%; N, 15.65%; P, 5.95%.

EXAMPLE 2

A stirred mixture of 3-acetylamino-4-(2'-bromo-4'-6'-dinitro phenylazo)-N,N-diethyl aniline (1 part), diethyl phosphite (0.44 part), tri-N-propylamine (0.86 part) and ethanol (33 parts) was boiled under reflux for 5 minutes. Cuprous iodide (0.21 part) was then added and the mixture was boiled under reflux for 1 hour. The mixture was cooled and the product was separated by filtration, washed with water and crystallized from ethanol to give 1.0 part of the product of Example 1.

EXAMPLE 3

A stirred mixture of 3-acetylamino-4-(2'-bromo-4',6'-dinitrophenylazo)-N,N-diethylaniline (4.7 parts), diphenyl phosphite (3.5 parts), cuprous iodide (1.0 part), sodium acetate (2.8 parts) and methyl alcohol (150 parts) was boiled under reflux for 30 minutes when thin layer chromatography showed reaction to be complete. The mixture was cooled and the product was separated and crystallised from methanol to give of dimethyl-3,5-dinitro-6-(2'-acetylamino-4'-diethylaminophenylazo)-phenylphosphonate [Found: C, 47.5; H, 5.1; N, 16.4; P, 6.2%. $C_{20}H_{25}N_6O_8P$ requires C, 47.25; H, 4.95; N, 16.55; P, 6.1%.]. Yield = 4.2 parts.

EXAMPLE 4

A stirred mixture of 3-acetylamino-4-(2'-bromo-4',6'-dinitrophenylazo)-N,N-diethylaniline (1.2 parts), diphenyl phosphite (0.9 parts), cuprous iodide (0.25 parts), sodium acetate (0.7 parts), and n-pentyl alcohol (40 parts) was heated at 90° C for 30 minutes when thin layer chromatography showed reaction to be complete. After removal of the solvent under reduced pressure, the residue was washed with water and crystallised from methanol to obtain di-n-pentyl-3,5-dinitro-6-(2'-acetylamino-4'-diethylaminophenylazo)-phenyl phosphonate [Found: C, 54.2; H, 6.7; N, 13.5; P, 5.2%. $C_{28}H_{41}N_6O_8P$ requires C, 54.2; H, 6.65; N, 13.55; P, 5.0%]. Yield = 1.24 parts.

EXAMPLE 5

When the 40 parts of n-pentyl alcohol used in Example 4 were replaced by 35 parts of n-heptyl alcohol the product obtained was di-n-heptyl-3,5-dinitro-6-(2'-acetylamino-4'-diethylaminophenylazo)-phenyl phosphonate.

EXAMPLE 6

A stirred mixture of 3-acetylamino-4-(2'-bromo-4',6'-dinitrophenylazo)-N,N-diethylaniline (1.2 parts), diethyl phosphite (0.5 part), tri-N-ethylamine (0.75 part)

and acetone (30 parts) was stirred at room temperature for 5 minutes. Cuprous iodide (0.25 parts) was then added and the mixture was stirred at room temperature for 1½ hours. The mixture was then poured into water (400 ml) and stirred for 3 hours.

The product was separated, washed with water and crystallized from methanol to give 1.21 parts of the product of Example 1.

EXAMPLE 7

If the cuprous iodide in Example 1 is replaced by 0.14 part of cuprous oxide, there are obtained 0.83 part of the azo dye.

EXAMPLE 8

A stirred mixture of 4-(2',4'-dibromo-6'-methylphenylazo)-N,N-diethylaniline (1.1 parts), diethyl phosphite, (0.5 part), sodium acetate (0.7 part), and ethanol (30 parts) was boiled under reflux for 5 minutes. Cuprous iodide (0.25 part) was then added and the mixture was refluxed for 1 hour. The mixture was cooled and poured into cold water (400 ml) and stirred for 3 hours.

The product was separated, washed with water and crystallized from methanol to give 1.12 parts of diethyl-3-methyl-5-bromo-2-[4'-N,N-diethylaminophenylazo]-phenyl phosphonate.

Found: C, 51.95%; H, 5.8%; N, 8.62%; P, 6.21%; Br, 16.57%. $C_{21}H_{29}BrN_3O_3P$ requires: C, 52.28%; H, 6.0%; N, 8.71%; P, 9.96%; Br, 16.60%.

EXAMPLE 9

A mixture of 2-bromo-acetophenone (0.5 part), diethyl phosphite (0.5 part), sodium acetate (0.7 part) and ethanol (30 parts) was boiled under reflux for 5 minutes. Cuprous iodide (0.25 part) was then added and the mixture was refluxed for 30 hours. The product was separated by distillation to give diethyl-2-acetylphenyl phosphonate.

EXAMPLE 10

A stirred mixture of 2-chlorobenzylamine (1.42 parts), cuprous iodide (0.2 part), sodium acetate (0.8 part), diethyl phosphite (2.8 parts) and ethanol (20 parts) was heated to the boil, and refluxing was continued for 30 hours. The product, which was a colorless oil, was shown by GLC to be substantially a single substance having by mass spectrometry a molecular weight of m/e = 242. This corresponds with the expected product diethyl-(o-aminomethylphenyl)phosphonate $C_{11}H_{17}NO_3P$.

What we claim is:

1. A process for the manufacture of aromatic phosphorus derivatives of the formula:

$Ar.PO(OR)_2$ (1)

where R is an optionally substituted alkyl, alkenyl, aralkyl, cycloalkyl or aryl radical, and Ar is an aromatic radical linked to the phosphorus atom through a carbon atom of the aromatic radical which comprises contacting a phosphorous acid diester of the formula:

$HO.P(OR)_2$ (2)

with an aromatic halide of the formula Ar—X in the presence of copper or a copper compound, an acid-binding agent and a solvent, the symbols R and Ar having the meanings stated above and X representing a halogen atom.

2. A process as claimed in claim 1 wherein there is used an aromatic halide in which the carbon-halogen bond is activated by an atom or group so structurally connected to the carbon atom as to have an electron-withdrawing effect.

3. A process as claimed in claim 1 wherein there is used as aromatic halide, an azo compound of the formula:

$Ar' - N = N - E$ wherein Ar' is a benzene or naphthalene radical having a halogen atom in ortho position to the azo group, and E represents the radical of a coupling component.

4. A process as claimed in claim 3 wherein Ar' is one of the radicals 2-chlorophenyl, 2-bromophenyl, 2-iodophenyl, 2-chloro-4-nitrophenyl, 2-bromo-4-cyanophenyl, 2,6-dichloro-4-nitrophenyl, 4,6-dinitro-2-chlorophenyl, 2-bromo-4-nitrophenyl, 2-bromo-4-nitro-6-methylsulphonylphenyl, 2,6-dibromo-4-nitrophenyl and 2-bromo-4,6-dinitrophenyl.

5. A process as claimed in claim 3 wherein the radical E carries a donor atom or group in ortho position to the azo group.

6. A process as claimed in claim 5 wherein the donor group is hydroxyl, amino, alkylamino, carboxylic acid, acylamino, alkylsulphonylamino, arylsulphonylamino, aralkylsulphonylamino or arylamino, or the donor atom is a member of a heterocyclic ring.

7. A process as claimed in claim 1 wherein there is used a copper compound selected from cuprous chloride and bromide, cupric chloride, copper bronze, cuprous acetate, cuprous benzoate, cuprous iodide, cupric sulphate, cupric acetate, tetrakis acetonitrile cuprous chloride, tetrakis acetonitrile cuprous trifluoromethyl sulphonate and tetrakis acetonitrile cuprous perchlorate.

8. A process as claimed in claim 1 wherein the solvent is an aliphatic or aromatic hydrocarbon, tetrahydrofuran, acetonitrile, dimethylformamide, an ester, an alkanol or a monoetherified alkandiol.

9. A process as claimed in claim 1 wherein there is used a solvent of the formula ROH and a phosphorus acid diester of formula $HO.P(OR)_2$ wherein R represents the same radical in both compounds.

10. A process as claimed in claim 1 wherein the phosphorous acid diester is diphenylphosphite and the solvent is an alcohol.

11. A process as claimed in claim 1 wherein the acid-binding agent is a tertiary amine of strongly basic character or the sodium or potassium salt of a weak acid.

* * * * *